(12) United States Patent
Dellimore et al.

(10) Patent No.: US 11,957,454 B2
(45) Date of Patent: Apr. 16, 2024

(54) DEVICE, SYSTEM AND METHOD FOR DETECTION OF PULSE AND/OR PULSE-RELATED INFORMATION OF A PATIENT

(71) Applicant: KONINKLIJKE PHILIPS N.V., Eindhoven (NL)

(72) Inventors: Kiran Hamilton J. Dellimore, Utrecht (NL); Jens Muehlsteff, Aachen (DE); Ralph Wilhelm Christianus Gemma Rosa Wijshoff, Munstergeleen (NL); Lars Schmitt, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 307 days.

(21) Appl. No.: 16/618,483

(22) PCT Filed: Jun. 22, 2018

(86) PCT No.: PCT/EP2018/066827
§ 371 (c)(1),
(2) Date: Dec. 2, 2019

(87) PCT Pub. No.: WO2018/234569
PCT Pub. Date: Dec. 27, 2018

(65) Prior Publication Data
US 2020/0100705 A1    Apr. 2, 2020

(30) Foreign Application Priority Data

Jun. 23, 2017 (EP) .................................. 17177582

(51) Int. Cl.
*A61B 5/11*   (2006.01)
*A61B 5/00*   (2006.01)
(Continued)

(52) U.S. Cl.
CPC ........ *A61B 5/1102* (2013.01); *A61B 5/02125* (2013.01); *A61B 5/02416* (2013.01);
(Continued)

(58) Field of Classification Search
None
See application file for complete search history.

(56) References Cited

U.S. PATENT DOCUMENTS 7,488,293 B2   2/2009 Marcovecchio et al.
9,872,638 B2 *  1/2018 Koivisto ............. A61B 5/6804
(Continued)

FOREIGN PATENT DOCUMENTS

WO   2016040262 A1   3/2016
WO   2016040263 A1   3/2016

OTHER PUBLICATIONS

M. Theodor et al., "Implantable acceleration plethysmography for blood pressure determination," 2013 35th Annual International Conference of the IEEE Engineering in Medicine and Biology Society (EMBC), Osaka, Japan, 2013, pp. 4038-4041, doi: 10.1109/EMBC.2013.6610431. (Year: 2013).*
(Continued)

*Primary Examiner* — Benjamin S Melhus

(57) ABSTRACT

The present invention relates to a device, system and method for detection of pulse and/or pulse-related information of a patient. To allow a single site solution, which is more robust to motion artefacts and arrhythmias, the device comprises an accelerometer signal input (51) configured to obtain an accelerometer signal acquired by an accelerometer sensor arranged at the patient's skin, a pulse signal input (52) configured to obtain a pulse-related signal of the patient, a patient information input (53) configured to obtain patient information, a model unit (54) configured to generate a model of accelerometer-based pulse palpation from the
(Continued)

pulse-related signal using said patient information and context information indicating the context of the acquisition of the accelerometer signal, a feature extraction unit (56) configured to extract one or more features from the accelerometer signal using the generated model and/or from the pulse-related signal, and a detection unit (57) configured to detect the pulse and/or pulse-related information of the patient from the one or more extracted features.

17 Claims, 5 Drawing Sheets

(51) Int. Cl.
*A61B 5/021* (2006.01)
*A61B 5/024* (2006.01)
(52) U.S. Cl.
CPC ........... *A61B 5/1116* (2013.01); *A61B 5/1118* (2013.01); *A61B 5/7225* (2013.01); *A61B 2562/0219* (2013.01); *A61B 2562/0238* (2013.01)

(56) References Cited

U.S. PATENT DOCUMENTS

| | | | |
|---|---|---|---|
| 10,973,410 B2* | 4/2021 | Marsh | G01J 5/0806 |
| 2004/0039420 A1 | 2/2004 | Jayne | |
| 2006/0084879 A1 | 4/2006 | Nazarian et al. | |
| 2011/0224498 A1* | 9/2011 | Banet | A61B 5/6824 600/300 |
| 2012/0215274 A1 | 8/2012 | Koh | |
| 2014/0221848 A1* | 8/2014 | Nagasaka | A61B 5/02438 600/479 |
| 2015/0112606 A1* | 4/2015 | He | A61B 5/4809 702/19 |
| 2015/0164351 A1* | 6/2015 | He | A61B 5/02125 702/19 |
| 2015/0265217 A1* | 9/2015 | Penders | A61B 5/681 600/300 |
| 2015/0305684 A1* | 10/2015 | Gross | A61B 5/7282 600/301 |
| 2016/0038045 A1 | 2/2016 | Shapiro | |
| 2017/0209053 A1* | 7/2017 | Pantelopoulos | A61B 5/02125 |
| 2017/0245767 A1* | 8/2017 | Ferber | A61B 5/0285 |
| 2017/0281024 A1* | 10/2017 | Narasimhan | A61B 5/6824 |
| 2017/0340209 A1* | 11/2017 | Klaassen | A61B 5/11 |
| 2017/0340219 A1* | 11/2017 | Sullivan | A61B 5/681 |
| 2018/0192888 A1* | 7/2018 | Yee | G16H 50/20 |
| 2020/0100705 A1 | 4/2020 | Dellimore | |

OTHER PUBLICATIONS

E. S. Winokur, et al., "A wearable vital signs monitor at the ear for continuous heart rate and Pulse Transit Time measurements," 2012 Annual International Conference of the IEEE Engineering in Medicine and Biology Society, San Diego, CA, USA, 2012, pp. 2724-2727, doi: 10.1109/EMBC.2 (Year: 2012).*

Babbs: "Oscillometric Measurement of Systolic and Diastolic Blood Pressures Validated in a Physiologic Mathematical Model"; Biomedical Engineering Online, vol. 11, Article No. 56, 2012.

Brearley et al: "Peripheral Pulse Palpation:An Unreliabvle Physical Sign"; Annals of the Royal College of Surgeons of England (1992), vol. 74, pp. 169-171.

Deakin et al: "Accuracy of the Advanced Trauma Life Support Guidelines for Predixctrng Systolic Blood Pressure Using Carotid, Femoral, and Radial Pulses: Observational Study"; BMJ vol. 321, Sep. 16, 2000, pp. 673-674.

Eberle et al: "Checking the Carotid Pulse Check: Diagnostic Accuracy of First Responders in Patients With and Without a Pulse"; Resuscitation, vol. 33, 1996, pp. 107-116.

Lundin et al: Distal Pulse Palpation:Is It Reliable?' World J. Surg. vol. 23, pp. 252-255, pp. 252-255.

Muehlsteff et al: "Feasibility of Pulse Presence and Pulse Strength Assessment During Head-Up Tilt Table Testing Using an AC Celerometer Located at the Carotid Artery";IEEE 2014, pp. 894-897.

Muehlsteff et al: "Pulse Detection With a Single Accelerometer Placed at the Carotid Artery: Performance in a Real-Life Diagnostic Test During Acute Hypotension"; IEEE 2015, pp. 434-437.

PCT/EP2018/066827 ISR & WO, Aug. 28, 2018, 15 Page Document.

Quan et al: "Myocardial Contraction Detection Using a CPR Feedback Sensor"; Resuscitation, 96S (2015) p. 17.

Zhang: "Arterial Waveform Measurement Using a Piezoelectric Sensor"; Department of Biomedical Engineering Virginia Commonwealth University, 2010, 66 Page Document.

* cited by examiner

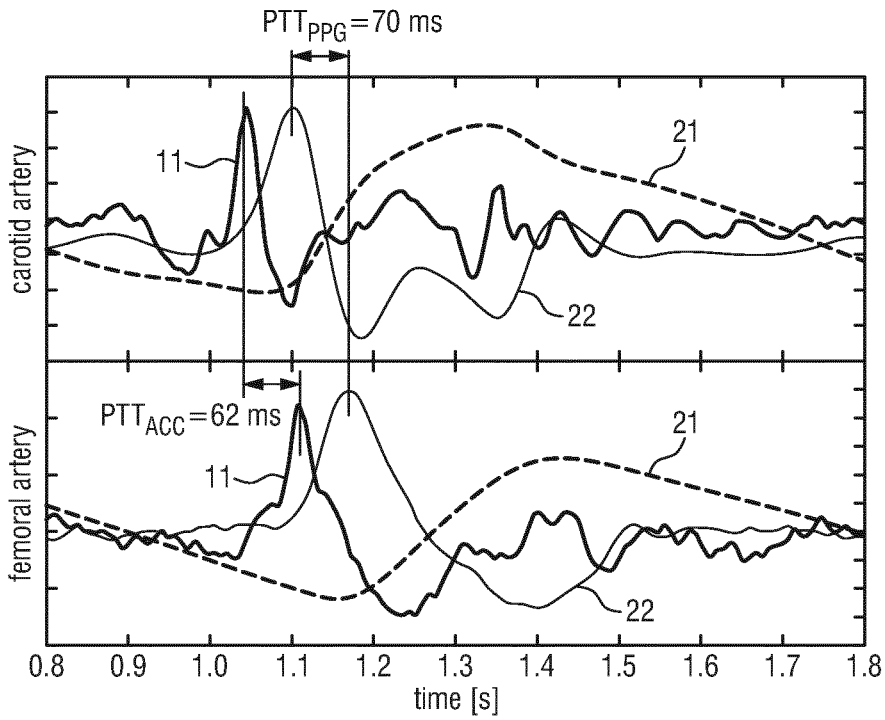
FIG.5A
FIG.5B
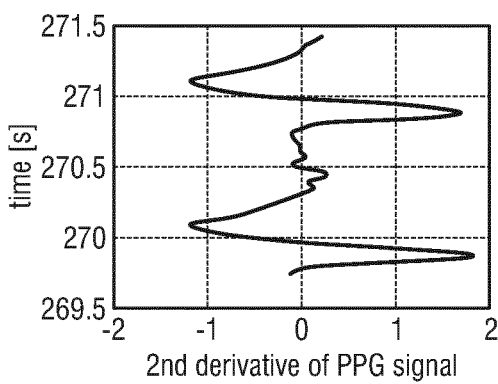
FIG.6A
FIG.6B
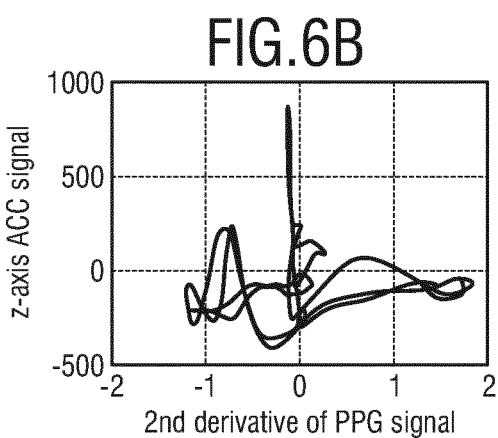
FIG.6C
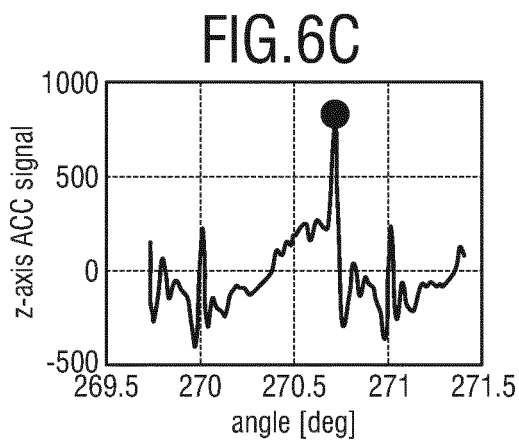

ature/placement. A single site solution therefore remains an unmet need not solved by the prior art. In addition, and more importantly, a solution, which is robust to motion artefacts and arrhythmias, has not yet been adequately addressed by the prior art.

DEVICE, SYSTEM AND METHOD FOR DETECTION OF PULSE AND/OR PULSE-RELATED INFORMATION OF A PATIENT

CROSS-REFERENCE TO PRIOR APPLICATIONS

This application is the U.S. National Phase application under 35 U.S.C. § 371 of International Application No. PCT/EP2018/066827, filed on Jun. 22, 2018, which claims the benefit of European Patent Application No. 17177582.8, filed on Jun. 23, 2017. These applications are hereby incorporated by reference herein.

FIELD OF THE INVENTION

The present invention relates to a device, system and method for detection of pulse and/or pulse-related information of a patient.

BACKGROUND OF THE INVENTION

Manual pulse palpation is widely used in clinical practice and emergency situations to assess the circulatory status of an individual for diagnostic and prognostic purposes. Among the many applications of manual pulse palpation include vascular disease diagnosis, spot check monitoring in the intensive care unit (ICU) and general ward to assess changes in patient condition, as well as in emergency medicine to determine the need to initiate or terminate cardiopulmonary resuscitation (CPR). Despite its ubiquity, previous work has shown that manual palpation is often unreliable and highly subjective, even when performed by trained healthcare professionals. A significant unmet clinical need therefore exists for a more objective and reliable method of pulse palpation.

An accelerometer (ACC) placed on the skin above the carotid artery can be used to detect the pulse, without needing to perform manual palpation. However, a major limitation of accelerometer-based palpation is the signal's susceptibility to motion artefacts, which may severely restrict the clinical settings in which it may be applied. This is also a problem that arises when accelerometers are used in the estimation of pulse-related information, such as pulse transit time (PTT) and pulse arrival time (PAT), which are surrogate measures of (changes in) blood pressure (BP). Hence there is a profound need for improving the motion robustness of accelerometer-based pulse palpation preferably by a simple-to-use and easy-to-apply technique.

In a recent publication (Quan W. and Herken U., "Myocardial contraction detection using a CPR feedback sensor", Resuscitation 2015; 96(S1):17) an approach is described which utilizes a cross-correlation function between ECG and accelerometer signals (i.e., the detected R-peaks of the ECG signal are used as time-reference points to support the detection of pulse events in the accelerometer waveform signal) to improve the pulse detection (i.e., myocardial contraction) performance of the accelerometer. While they reported reasonably good performance (sensitivity and specificity of about 0.7), a major drawback of this approach is that it requires placement of ECG electrodes on the individual (i.e. the patient) and an accelerometer sensor at a different site, which may not always be feasible in some situations and requires more time-consuming sensor attachment/placement. A single site solution therefore remains an unmet need not solved by the prior art. In addition, and more importantly, a solution, which is robust to motion artefacts and arrhythmias, has not yet been adequately addressed by the prior art.

Furthermore, current state of the art devices and methods for pulse palpation with ACC and pulse-related signals, such as photoplethysmography (PPG) signals, use ACC signals as reference signals, i.e. helper signals, in PPG-based pulse palpation. Accordingly, these methods mostly focus on a patient's microcirculation for pulse palpation.

WO 2016/040263 A1 discloses wrist-worn devices and related methods to measure a pulse transit time non-invasively and calculate a blood pressure value using the pulse transit time. The disclosed wrist-worn device includes an accelerometer, a photoplethysmogram (PPG) or a pulse pressure sensor, and a controller.

US 2004/0039420 A1 discloses a pulse detection apparatus, software, and method that uses signal data obtained from an accelerometer placed on a patient's body to detect the presence of a cardiac pulse. The accelerometer is adapted to sense movement due to a cardiac pulse and produce accelerometer signal data in response thereto. Processing circuitry analyzes the accelerometer signal data for a feature indicative of a cardiac pulse and determines whether a cardiac pulse is present in the patient based on the feature.

US 2012/0215274 A1 discloses an implantable medical device ("IMD") that processes and analyzes valuable clinical information regarding cardiac performance. A database or correlator is pre-customized to the specific patient, by correlating signals received by a remote accelerometer associated with heart movements with accurate heart sounds recorded from a microphone to provide a more effective and customized basis for estimating heart sound. The information is then used to better control an implantable medical device.

SUMMARY OF THE INVENTION

It is an object of the present invention to provide a device, system and method for detection of pulse and/or pulse-related information of a patient, which allow a single site solution, which is more robust to motion artefacts and arrhythmias.

In a first aspect of the present invention a device for detection of pulse and/or pulse-related information of a patient is presented comprising:

an accelerometer signal input configured to obtain an accelerometer signal acquired by an accelerometer sensor arranged at the patient's skin, a pulse signal input configured to obtain a pulse-related signal of the patient, in particular from a pulse signal sensor, a patient information input configured to obtain patient information, in particular from a patient information source, a model unit configured to generate a model of accelerometer-based pulse palpation using the pulse-related signal as a reference signal and further using said patient information and context information indicating the context of the acquisition of the accelerometer signal, a feature extraction unit configured to extract one or more features from the accelerometer signal using the generated model and/or from the pulse-related signal, and a detection unit configured to detect the pulse and/or pulse-related information of the patient from the one or more extracted features.

In a further aspect of the present invention a system for detection of pulse and/or pulse-related information of a patient is presented comprising:

an accelerometer signal sensor configured to be arranged at the patient's skin and to acquire an accelerometer signal, a pulse signal sensor configured to be arranged at the patient's skin and to acquire a pulse-related signal of the patient, a patient information source configured to provide patient information, and a device for detection of pulse and/or pulse-related information of a patient as disclosed herein configured to detect pulse and/or pulse-related information of the patient based on the accelerometer signal, the pulse-related signal and the patient information.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed system, in particular as defined in the dependent claims and as disclosed herein.

The present invention is based on the idea to utilize a pulse-related signal, e.g. a photoplethysmography (PPG) signal, as reference signal to provide motion robust feature extraction from the accelerometer signal for the purpose of pulse presence detection and/or pulse-related information (such as pulse strength, PTT or PAT) measurement. In other words, identification of cardiac pulses is performed using an accelerometer signal, wherein a pulse-related signal is additionally used to support pulse palpation. From the accelerometer signal morphology there may be detected a pulse itself, but also its strength and other pulse-related features. In the course of this detection a pulse-related signal may be used to support said detection, in particular to acquire a more refined detection. This may be accomplished by cross-correlation (or other means) of features in the accelerometer and pulse-related signals acquired, preferably, at the same site or other location. The present invention thus enables reliable detection of characteristic features in the accelerometer signal, in particular during challenging physiological conditions such as arrhythmias or during phases of large motion e.g. during cardiopulmonary resuscitation.

While pulse palpation according to the present invention may be focused on a patient's microcirculation (meaning that the accelerometer signal and pulse-related signal are acquired from corresponding body sites such a s wrist, for example), pulse palpation may particularly be performed using accelerometer signals and pulse related signals which are from larger arteries close to the skin surface, such as the carotid.

The proposed device, system and method thus may rely on sensor placement at a single anatomical site for motion and arrhythmia robust accelerometer-based pulse presence detection. Further, reliable, highly sensitive and specific, motion and arrhythmia robust accelerometer-based pulse detection is enabled. Still further, the present invention does not require electrode placement for improving motion and arrhythmia robustness in accelerometer-based pulse detection. Finally, estimation of blood pressure ranges and changes from a single anatomical site during cardiopulmonary resuscitation may be enabled. Using an ECG signal as in known methods is less preferred for improved feature extraction, since two signals of different origin (ECG caused by electrical activation of the heart) and accelerometer (caused by mechanical dilatation of an artery due to propelled blood from the heart) are mixed in a correlation process.

Generally, said pulse signal sensor comprises one or more of a PPG sensor, an ECG sensor, an arterial blood flow sensor, an ultrasonic sensor and a radar sensor. In a preferred embodiment, however, said pulse signal input is configured to obtain a PPG signal as pulse-related signal of the patient.

In an embodiment the proposed device further comprises a context information generation unit configured to generate said context information indicating the context of the acquisition of the accelerometer signal from said accelerometer signal, in particular including one or more of posture, activity, motion, and treatment phase of the patient. The context information may generally be provided as input, e.g. from a sensor or other detection means for detecting it, but it may also be directly generated within the device, which may thus comprise a corresponding context information generation unit, e.g. an image processing unit that processes images, e.g. obtained by a camera, to detect the context information. The context information may also be generated from the accelerometer signal. The use of such context information further improves the reliability and robustness against motion.

The patient information input may be configured to obtain patient information including one or more of age, gender, weight, height, externally applied pressure, heart rate, pulse pressure, and systolic blood pressure. Such information may e.g. be provided from respective sensors or an interface, at which the patient or another person, e.g. a caregiver, enters such information. The patient information may also be obtained from a patient information system, e.g. an electronic health record of a hospital or doctor.

The model unit may be configured to additionally use artery characteristics and/or a predetermined pulse template in the generation of the model. The model may e.g. be a physical model of accelerometer-based palpation. The accelerometer signal is the second derivative of the artery dilatation signal detected by the accelerometer sensor. This dilatation signal depends on artery stiffness, artery size and artery location. Knowledge or inference e.g. from body characteristics of these artery parameters and the sensor locations allow to estimate an ideal (noiseless) and expected accelerometer signal serving as template for improved feature extraction derived from a physical model.

As mentioned above, in an embodiment said detection unit is configured to detect if pulse is present and/or to detect pulse arrival time and/or pulse transit time as pulse-related information. This embodiment thus provides valuable information in very short time and with low efforts, e.g. in an emergency situation.

In a practical implementation said feature extraction unit is configured to extract one or more features from the accelerometer signal by comparing the obtained accelerometer signal, in particular accelerometer signal components in three orthogonal directions, with the generated model.

Said feature extraction unit may further be configured to cross-correlate one or more features of a 2D representation between the obtained accelerometer signal and the obtained pulse-related signal, in particular the second derivative of the obtained pulse-related signal. A 2D representation plots one signal versus the other signal. This allows for the detection of specific patterns, which may not be obvious when using two individual signal plots versus time. The 2D signal representation is not from a signal acquired at a second site on the body, but is rather a signal stored in memory, i.e., an already acquired accelerometer and PPG signals or derived features.

Said feature extraction unit may also be configured to cross-correlate an angle or area between one or more features of the obtained accelerometer signal and the obtained pulse-related signal, in particular the second derivate of the obtained pulse-related signal. For instance, by making a 2D plot of the obtained accelerometer signal and the obtained pulse-related signal or a derivative of the obtained pulse-related signal, an angle or phase-shift or time-delay between features can be determined. Furthermore, the 2D plot reveals trajectories of features, of which the spanned area can be determined, which can be discriminative as well. Such 2D plots can reveal discriminative aspects which are less clear in other representations of the features.

Still further, in an embodiment said feature extraction unit may be configured to high-pass filter the accelerometer signal and to compare one or more features of the high-pass filtered accelerometer signal with the pulse-related signal, in particular using dynamic time-warping (i.e., non-linearly stretching or shrinking of the time series in the time direction). Dynamic time-warping finds an optimal match between two sequences, e.g., time-series, by non-linearly stretching or shrinking the sequences in the time direction. This method can accommodate for differences in the duration of the pulse-shape in the pulse-related signal (e.g. the PPG signal) and the accelerometer signal. High-pass filtering is advantageous to reduce noise (i.e., boost SNR) by cutting lower frequencies and focusing on frequencies relevant to the pulse frequency. For instance, by high-pass filtering the signals first, the dynamic time-warping is not compromised by baseline wander possibly present in the signal.

The detection unit may be configured to use pulse intervals and/or pulse amplitudes detected in the accelerometer signal and the pulse-related signal in the detection of pulse and/or pulse-related information.

BRIEF DESCRIPTION OF THE DRAWINGS

These and other aspects of the invention will be apparent from and elucidated with reference to the embodiment(s) described hereinafter. In the following drawings:

FIG. 5A shows a diagram illustrating feature extraction using signals acquired by sensors located at the carotid site, FIG. 5B shows a diagram illustrating feature extraction using signals acquired by sensors located at the femoral site, FIG. 6A shows a diagram of the 2nd derivative of the PPG signal acquired at the femoral artery versus time, FIG. 6B shows a 2D representation of the 2nd derivative of the PPG signal versus the z-axis of the accelerometer (ACC) signal, FIG. 6C shows a diagram of the z-axis of the accelerometer (ACC) signal versus time.

DETAILED DESCRIPTION OF THE EMBODIMENTS

Figure 1:
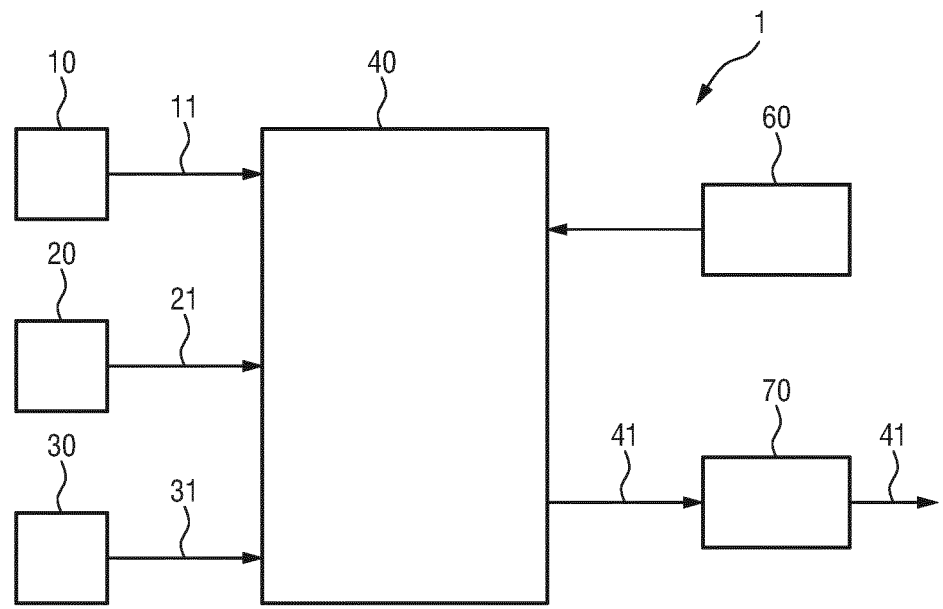
FIG. 1 shows a schematic diagram of a first embodiment of a system for detection of pulse and/or pulse-related information of a patient according to the present invention.

FIG. 1 shows a schematic diagram of a first embodiment of a system 1 for detection of pulse and/or pulse-related information of a patient according to the present invention. The system comprises an accelerometer (ACC) signal sensor 10 configured to be arranged at the patient's skin and to acquire an accelerometer (ACC) signal 11 and a pulse signal sensor 20 configured to be arranged at the patient's skin and to acquire a pulse-related signal 21 of the patient. The ACC signal sensor 10 may e.g. include an accelerometer and the pulse signal sensor 20 may include one or more of a PPG sensor, an ECG sensor, an arterial blood flow sensor, an ultrasonic sensor or a radar sensor. Preferably, both the ACC signal sensor 10 and the pulse signal sensor 20 are arranged at a single, fixed anatomical location on the patient's body. For this purpose they may be combined into a single sensor unit, which is e.g. provided with some means for attachment to the patient's skin, such as an adhesive sticker or strap. A preferred location to attach the ACC signal sensor 10 and the pulse signal sensor 20 is above the carotid or femoral artery, since they are large central arteries close to the skin surface.

The system 1 further comprises a patient information source 30 configured to provide patient information 31. Such patient information may include one or more of age, gender, weight, height, externally applied pressure, heart rate, pulse pressure, and systolic blood pressure. The patient information source may include a hospital's database, a doctor's record, a user interface or a combination of one or more those items.

The system 1 further comprises a device 40 configured to detect pulse and/or pulse-related information 41 of the patient based on the ACC signal 11, the pulse-related signal 21 and the patient information 31. The device 40 may be implemented in hard- and/or software, e.g. as a programmed CPU, computer, processor, etc. The device 40 may be integrated into a common unit with the ACC signal sensor 10 and the pulse signal sensor 20, but may alternatively be arranged at a distant location, to which the ACC signal 11 and the pulse-related signal 21 are transferred, e.g. through wired or wireless communication, e.g. via network, Bluetooth, Wi-Fi, etc.

The system 1 may further comprise a power supply 60, e.g. a battery, for supplying the various elements with necessary power, and an output unit 70, e.g. a display such as a coarse LED array, an e-ink display screen, etc., for issuing the result of the detection, i.e. the detected pulse and/or pulse-related information 41, for instance to indicate the presence or absence of a pulse to a user.

Figure 2:
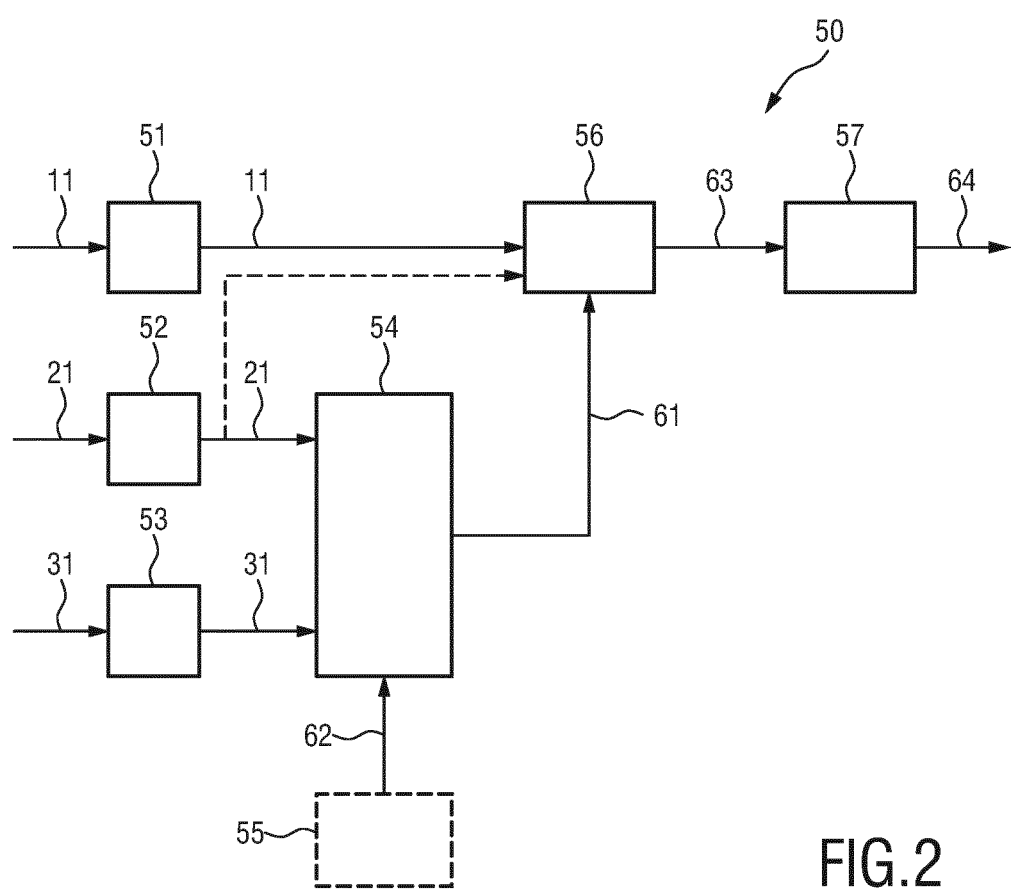
FIG. 2 shows a schematic diagram of a first embodiment of a device for detection of pulse and/or pulse-related information of a patient according to the present invention, FIG. 3 schematically illustrates the basic building blocks of a physical model and the key parameters included in a model step.

FIG. 2 shows a schematic diagram of a first embodiment of a device 50 for detection of pulse and/or pulse-related information of a patient according to the present invention, which may be used as device 40 in the system 1 shown in FIG. 1. The device 50 comprises various inputs, including an ACC signal input 51 configured to obtain the ACC signal 11 acquired by the ACC sensor 10 arranged at the patient's skin, a pulse signal input 52 configured to obtain the pulse-related signal 21 of the patient, and a patient information input 53 configured to obtain the patient information 31. The inputs may be implemented as data interfaces for directly or indirectly obtaining (i.e. receiving or retrieving) the respective signals from the sensors 10, 20 and the patient information source 30, respectively. The data interfaces may be wired or wireless interfaces, such as network interfaces, communication interfaces, and may also be implemented as a single common interface.

The device 50 further comprises a model unit 54 configured to generate a model 61 of ACC-based pulse palpation from the pulse-related signal 21 using said patient information 31 and context information 62 indicating the context of the acquisition of the ACC signal. The model assumes the detection of the radial acceleration component due to arterial dilatation detected above an underlying artery from a passing pressure wave (produced by the ejection of blood from the heart). Model parameters include age, externally applied contact pressure (cP), gender, HR, Pulse Pressure and SBP. The arterial pressure waves, which serve as model input, can be either obtained from a measured arterial BP signal or can be modeled BP wave, e.g., based on a Fourier-series approach. The model allows insight into basic signal properties and their dependencies from hemodynamic parameters which are relevant to pulse palpation.

The context information 62 may be provided as additional input, e.g. from an external context information providing unit (not shown). Alternatively, an optional context information generation unit 55 may be provided as part of the device 50 that is configured to generate said context information indicating the context of the acquisition of the ACC signal from said ACC signal, in particular including one or more of posture, activity, motion, and treatment phase of the patient. The external context information providing unit and the context information generation unit 55 may be configured e.g. to evaluate the given signals, e.g. the ACC signal 11, or any additional signals, such as camera images, to detect the desired context information. For instance, from the ACC signal 11 the posture, activity and motion may be derived. The treatment phase may be obtained from treatment information, e.g. recorded in an electronic health record.

The device 50 further comprises a feature extraction unit 56 configured to extract one or more features 63 from the ACC signal using the generated model and/or from the pulse-related signal. Said features are preferably characteristic features in the time domain, frequency or time-frequency domain. Characteristic features may comprise: peaks, root-mean-square, standard deviation, maximum frequency, prominence, etc. One approach to use the generated model is to correlate the generated template signal with the measured signal. Features from the correlation can be used such as correlation coefficients at different time lags, prominence or time lags e.g. to extract a pulse transit time. Another approach is to use the template to constrain search windows for features in the measured signal.

The device 50 further comprises a detection unit 57 configured to detect the pulse and/or pulse-related information 64 of the patient from the one or more extracted features. Various embodiments can be used for implementing the detection, which will be explained below in more detail.

An aspect of the present invention is to extract features in the ACC signal, acquired preferably at a central site, e.g., the carotid or femoral artery, based on cross-correlation (or other means) with features in the PPG signal (as a preferred example for the pulse-related signals, which will be used in the subsequent explanations) acquired at the same site or other location, in order to improve motion and arrhythmia robustness of ACC based pulse detection and PTT/PAT estimation from the ACC signals. This may be accomplished in the following ways used in preferred embodiments.

Figure 3:
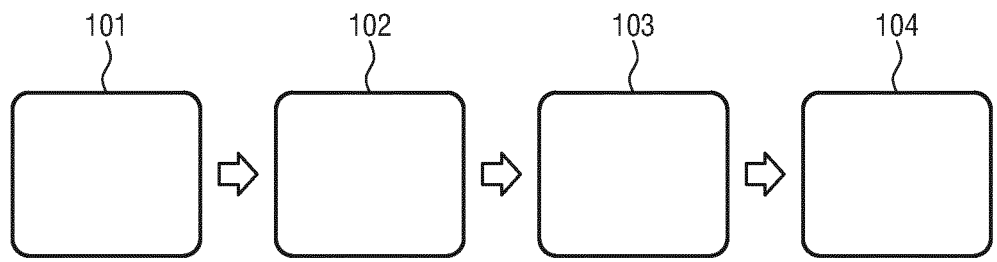
Figure 4:
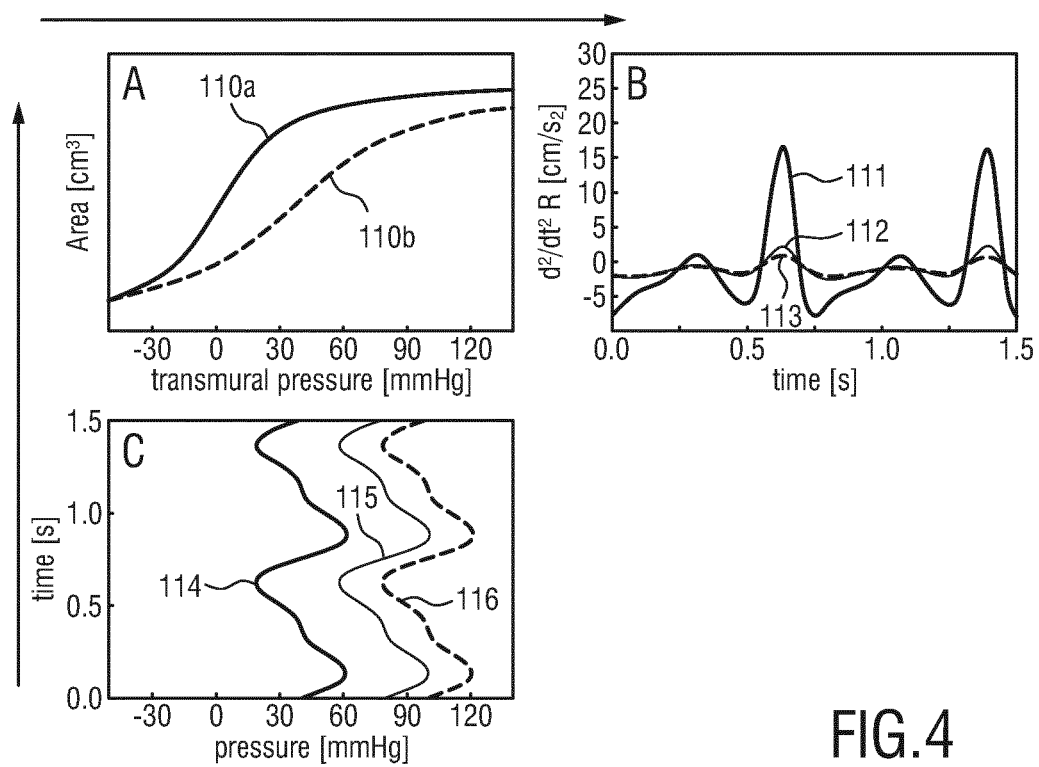
FIG. 4 shows a diagram of signals used in the model step.

FIG. 3 schematically illustrates the basic building blocks of a physical model and the key parameters included in the model step performed by the model unit 54. The implemented physical model has been developed to gain insight into basic signal properties and their dependencies from hemodynamic parameters. FIG. 4 shows a diagram of signals used in the model step. The building blocks include using the arterial pressure pulse (block 101), transforming it into an area change of the vessel (block 102), obtaining the radius of the artery (block 103) and using the second derivate to estimate acceleration (block 104). FIG. 3 shows a block diagram of the implemented physical model which has been developed to gain insight into basic signal properties and their dependencies from hemodynamic parameters FIG. 4A illustrates the age and gender dependence of transmural pressure, in particular the pressure-volume curve, which relates the blood pressure wave (with cP=0 assumed in the plot) to artery dimensions, where the response depends on age and gender. The signal 110a is for an 80 year old individual and the signal 110b is for a 40 year old individual. FIG. 4B shows the second derivative 111, 112, 113 of the radius ($d^2/dt^2$ R) for different values of SBP, in particular how the arterial diameter changes (based on the non-linear transfer function in plot A) at different SBPs (60, 100 and 120 mmHg) for an 80 year old individual. FIG. 4C shows SBP pressure signals 114, 115, 116 over time corresponding to the second derivatives 111, 112, 113, in particular simulated BP waves of three different SBP of 120 mmHg, 100 mmHg and 60 mmHg at a constant PP of 40 mmHg and a HR of 60 bpm.

An ACC sensor placed at a central, easily accessible site, preferably the carotid or femoral artery, and a PPG sensor placed at the same site or another anatomical location are used to acquire signals (i.e. ACC signal 11 and pulse-related signal 21) relevant to the measurement of a physiological parameter, such as the pulse, PAT or PTT. The acquired signals 11, 21 are then used as input to a physical model of ACC-based palpation, which can be run on a CPU processor. The entire system may be powered with a battery or similar means and can be easily attached to the skin at a given anatomical location. Model parameters include but are not limited to: age, externally applied contact pressure, gender, weight, height, HR, PP, and SBP (systolic blood pressure). Arterial pressure waves, which serve as a model input, can be either obtained from a measured arterial BP signal or can be a modeled BP wave, e.g. based on a Fourier-series approach. This is for example described by C. F. Babbs, "Oscillometric measurement of systolic and diastolic blood pressures validated in a physiologic mathematical model", BioMedical Engineering Online, 2012, vol. 11, pp. 56.

Robust features in the ACC signal relevant to pulse and PTT/PAT may be extracted by comparing the measured ACC signal to the output of the physical model, by finding characteristic signal features in the time domain or by cross-correlation of the ACC and PPG signal time series. Example features from a cross-correlation may be, e.g., peak prominence or phase shifts from peak structures in the correlation signal. Also, FIG. 5 shows pulse transit times extracted from the ACC signals ($PTT_{ACC}$) and the second derivatives of the PPG signals ($PTT_{PPG}$) based on time instances detected via the maximum amplitudes within a pulse in the time domain ACC signal 11 and the PPG signal 21 acquired by sensors located at the carotid site (FIG. 5A) or, alternatively, at the femoral site (FIG. 5B). In FIG. 5 it can be seen that the second derivative 22 of the PPG signal 21 has a similar morphology as the z-axis ACC signal morphology, for both anatomical sites (i.e., the carotid and femoral artery), which enables easy feature extraction via cross-correlation.

In an alternative embodiment, another approach to the cross-correlation method may be used in which an angle or area between the PPG signal feature (e.g. the second derivative of the PPG signal) and an ACC feature may be used for feature extraction and to ensure motion and arrhythmia robustness. This is illustrated in FIG. 6. For instance, by making a 2D plot of the obtained ACC signal and the obtained pulse-related signal or a derivative of the obtained pulse-related signal, an angle or phase-shift or time-delay between features can be determined. Furthermore, the 2D plot reveals trajectories of features, of which the spanned area can be determined, which can be discriminative as well. Such 2D plots can reveal discriminative aspects which are less clear in other representations of the features. For instance, each heart beat will result in an orbit in the 2D plot, but the duration of the orbit is not a direct parameter in this plot, which can make such a 2D plot more robust against variations in the pulse rate (i.e., arrhythmias). Other PPG features may also be used to achieve this. It is important to note here that the angle or area is position dependent.

FIG. 6 shows a diagram illustrating feature extraction in the ACC signal based on the angle or area between features in the ACC and PPG signals. FIG. 6A shows the 2nd derivative of the PPG signal acquired at the femoral artery versus time. FIG. 6C shows the z-axis of the ACC signal versus time. FIG. 6B illustrates the 2D representation of these signals, with the 2nd derivative of the PPG signal on the horizontal axis, and the z-axis of the ACC signal on the vertical axis. FIG. 6B shows that local maxima in the z-axis of the ACC signal occur just before a negative-to-positive zero-crossing in the 2nd derivative of the PPG signal. The angle between the local maximum and the vertical axis in the 2D representation gives information about the phase relationship between the z-axis accelerometer signal and the 2nd derivative of the PPG signal.

In an alternative embodiment, the features of the PPG signal are compared to features of the high-pass filtered double-integrated ACC signal. As the differentiation operation can boost high-frequency noise, comparison of the high-pass filtered double-integrated ACC and the PPG signal may enhance the performance. Also in this approach, the appearance of both signals is first made comparable, after which (features in) the signals are compared.

In yet another alternative embodiment, similarity between the second derivative of the PPG signal and the ACC signal, or between the PPG signal and the high-pass filtered double-integrated ACC signal, is determined via dynamic time warping. Dynamic time-warping finds an optimal match between two sequences, e.g., time-series, by non-linearly stretching/shrinking the sequences in the time direction. This method can accommodate for differences in the duration of the pulse-shape in the PPG and the ACC signals. To properly compare the pulses in the ACC and PPG signals, they may be normalized to unit amplitude first.

In yet another alternative embodiment, more robust detection of arrhythmias is achieved via more detailed analysis of the PPG and ACC signal waveform. If a pulse arrives earlier, it is expected to have a smaller amplitude in the PPG and ACC signals, and the following delayed pulse is expected to have a larger amplitude in the PPG and ACC signals. By simultaneous analysis of the pulse intervals and the pulse amplitudes, arrhythmia detection can be made more reliable. That is, if an arrhythmia is an "early pulse" followed by a "late pulse" and the amplitudes of the two involved pulses are smaller and larger than the average amplitudes, respectively, this strengthens the assumption that it concerns an arrhythmia and not an artifact.

Figure 7:
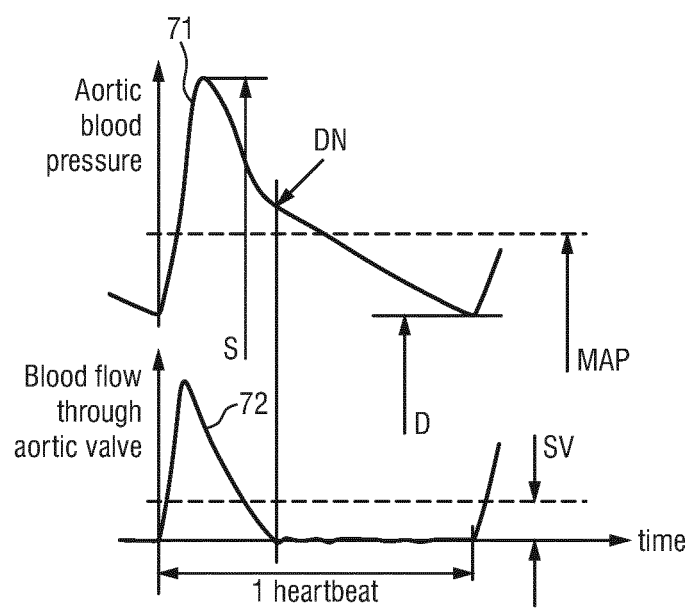
FIG. 7 shows an example of the aortic blood pressure waveform and the blood flow waveform over one heartbeat interval.

In an alternative embodiment a sensor measuring local arterial blood flow is used instead of the PPG sensor. As an example, an ultrasonic sensor or radar sensor can be used to measure blood flow. FIG. 7 shows an example of the aortic blood pressure waveform 71 and the blood flow waveform 72 (blood flow through the aortic valve) over one heartbeat interval. It can be seen that the main peaks of the two signals 71, 72 correlate well, which can be used for feature extraction. It should be noted that the aorta serves as an example in this illustration. For the sensors considered in this invention arteries close to the skin are mainly of relevance. Hereby, DN indicates the dicrotic notch (which coincides with the aortic valve closure), S indicates SBP, D indicates DBP and SV indicates stroke volume (i.e., the volume of blood pumped from the left ventricle per beat found by integrating the flow over one beat.) The blood flow waveform over one heartbeat interval provides additional features to be extracted in the ACC signal which correspond to important blood flow related parameters of interest such as stroke volume and aortic valve closure etc.

In an alternative embodiment three sensors measuring different physiological quantities at the same location may be used for cross-correlation. For example, waveform measurements of blood flow (measured with an ultrasound or radar sensor), blood volume (measured with a PPG sensor), and skin surface acceleration due to artery dilatation (measured with a ACC sensor) can be cross-correlated for improved, in particular, more robust feature extraction.

In an alternative embodiment a multitude of sensors measuring the same physiological quantities at slightly different locations may be used for cross-correlation. For example, an array or matrix of ACC sensors can be used. Preferably, in such an embodiment the individual sensor elements of the array or matrix are mechanically decoupled (at least in z-direction). By cross-correlation of the measured signals, the extraction of signal features is improved. E.g. the sensor element with the strongest peak can be used for feature extraction (selection diversity) or by combining multiple signals of adjacent sensors. As an effect the overall sensor placement can be significantly eased, as pulse detection becomes more robust against slight misplacement of the sensor device.

The above outlined approaches can be used to achieve improved motion robust ACC pulse detection and/or PAT/PTT estimation for the following reasons:

i) the different sensors may have different sensitivities to motion which means that even if one signal (e.g., from the ACC) is influenced by motion the other signal (e.g. from the PPG) may be less affected thereby enabling easier feature extraction;

ii) key features which may not be readily apparent in any one signal can be more easily identified from the comparison of both the PPG and ACC signals and thereby correlated or referenced even under conditions of moderate to high motion.

Figure 8:
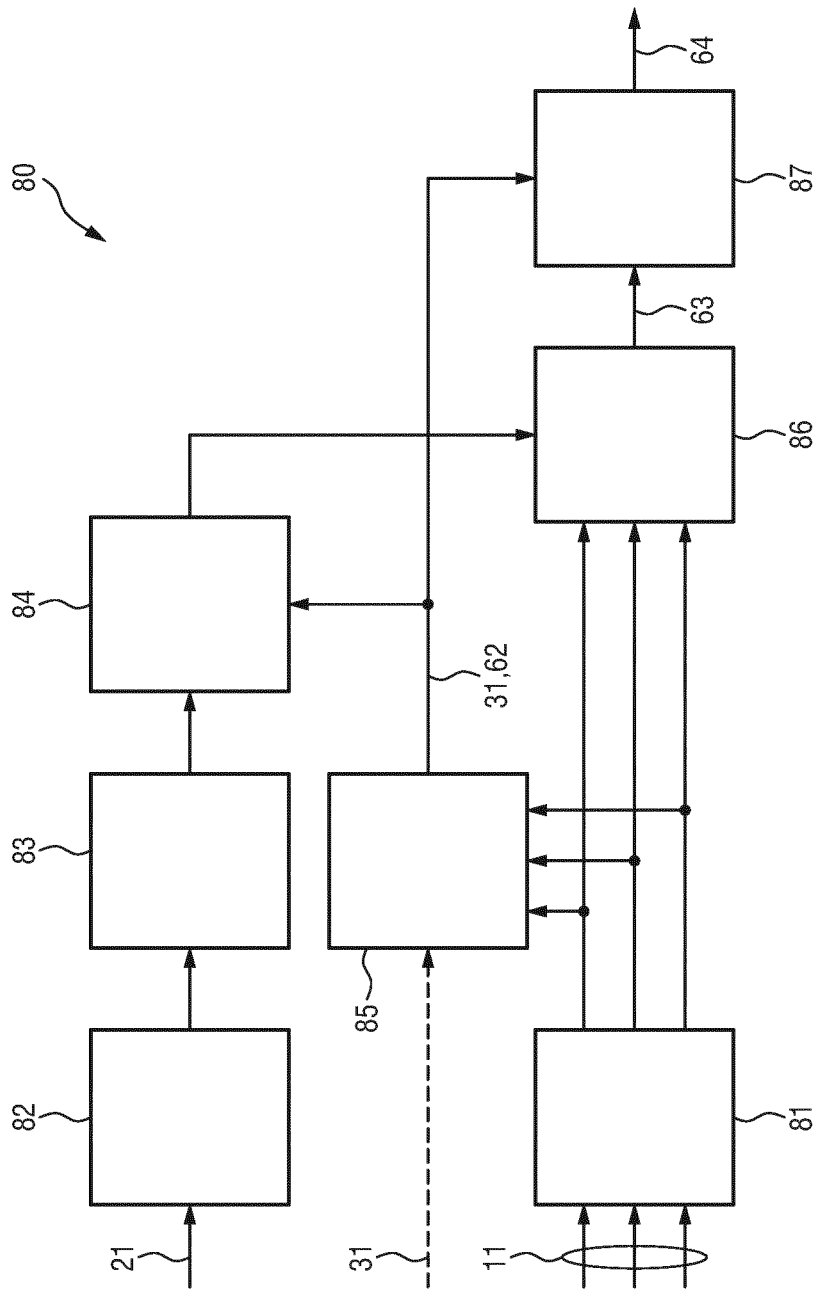
FIG. 8 shows a schematic diagram of a possible implementation of the proposed method.

FIG. 8 shows a schematic diagram of a possible implementation of the proposed method 80, which is described in more detail. Inputs to the method (and the corresponding device) are a PPG signal 21, a 3-axis ACC signal 11 and a-priori information 31 of the patient. Both signals 11, 21 might be pre-processed (blocks 81, 82) by standard techniques such as filtering, normalization, offset-correction or alike. In particular, the ACC signal 11 may also be preprocessed (e.g., filtered) to eliminate or minimize contamination of the acquired arterial dilatation signal by the ballistocardiogram (BCG) signal.

From the PPG signal 21 the pulse rate is extracted (beat-series extraction from feature points; block 83) as one of the inputs for generating a template signal for the acceleration signal. The other input for the template generation (block 84) is context-information 31 related to the patient such as age, gender, etc. as well as other context information 62 relating to posture, activity or treatment phase (e.g., measurement during CPR or at rest), which may be obtained (block 85) from the ACC signal 11. Based on these input parameters, an expected template of the acceleration signal is generated (block 84), which is then used for improved feature extraction (block 86) using techniques as discussed above. In a final step (block 87) the more robust feature 63 and the context information 31, 62 can be used in a classifier to infer the patient status 64 such as "pulse presence" or "ROSC" (return of spontaneous circulation).

It should be noted that the role of the PPG signal and the acceleration signal can also change, so that the acceleration signal serves as input to generate a template for a PPG signal. Also, it is possible for the ECG signal to be used instead of the PPG signal if it is available (e.g., if AED pads are connected).

The present invention can find application to pulse presence detection for the diagnostic and prognostic clinical assessment of the circulatory status of an individual. The many applications of manual pulse palpation include vascular disease diagnosis, spot check monitoring in the intensive care unit (ICU) and general ward to assess changes in patient condition, as well as in emergency medicine to determine the need to initiate or terminate cardiopulmonary resuscitation (CPR). It is also useful for PTT and PAT assessment, which serves as a surrogate measure of blood pressure. Therefore, it may be relevant for a patient monitor.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for reducing motion artefacts in a detection of at least one of pulse or pulse-related information of a patient, the device comprising:

an accelerometer signal input configured to obtain an accelerometer signal acquired by an array of accelerometer sensors arranged at skin of the patient;

wherein the accelerometer sensors are configured to directly contact the skin via an adhesive layer or a fastening strap;

where the accelerometer sensors are mechanically decoupled in at least one direction;

wherein the accelerometer signal input is configured to measure a skin surface acceleration with the accelerometer sensors;

wherein the accelerometer signal input is configured to combine signals from the array of accelerometer sensors to obtain the accelerometer signal from the skin surface acceleration;

a pulse signal input configured to obtain a pulse-related signal of the patient from a pulse signal sensor;

a patient information input configured to obtain patient information from a patient information source;

a display;

one or more computer processors;

and a non-transitory storage medium storing instructions that, when executed by the one or more computer processors, cause the one or more computer processors to:

generate a template accelerometer signal that models accelerometer-based pulse palpation using the pulse-related signal as a reference signal and further using the patient information and context information indicating context of the acquisition of the accelerometer signal;

extract one or more features from the accelerometer signal by comparing the accelerometer signal to the generated template accelerometer signal;

detect the pulse and pulse strength of the patient from the one or more extracted features;

and display on the display a presence of the pulse and the pulse strength.

2. The device as claimed in claim 1, wherein the pulse signal input is configured to obtain a PPG signal as the pulse-related signal of the patient.

3. The device as claimed in claim 1, wherein the instructions further cause the one or more computer processors to generate the context information indicating the context of the acquisition of the accelerometer signal from the accelerometer signal, the context information including one or more of a posture, an activity, a motion, and a treatment phase of the patient.

4. The device as claimed in claim 1, wherein the patient information input is configured to obtain patient information including one or more of age, gender, weight, height, externally applied pressure, heart rate, pulse pressure and systolic blood pressure.

5. The device as claimed in claim 1, wherein the instructions further cause the one or more computer processors to additionally use at least one of artery characteristics or a predetermined pulse template in the generation of the template accelerometer signal.

6. The device as claimed in claim 1, wherein the instructions further cause the one or more computer processors to detect when the pulse is present and/or to detect at least one of a pulse arrival time or a pulse transit time as pulse-related information.

7. The device as claimed in claim 1, wherein the instructions further cause the one or more computer processors to compare the accelerometer signal in three orthogonal directions with the generate template accelerometer signal.

8. The device as claimed in claim 1, wherein the instructions further cause the one or more computer processors to high-pass filter the accelerometer signal and to compare one or more features of the high-pass filtered accelerometer signal with the pulse-related signal using dynamic time-warping.

9. The device as claimed in claim 1, wherein the instructions further cause the one or more computer processors to use at least one of pulse intervals or pulse amplitudes detected in the accelerometer signal and the pulse-related signal in the detection of the pulse or the pulse strength of the patient.

10. A method for reducing motion artefacts in detection of at least one of pulse or pulse-related information of a patient, the method comprising:
obtaining an accelerometer signal acquired by an array of accelerometer sensors arranged at skin of the patient;
wherein the accelerometer sensors are configured to directly contact the skin via an adhesive layer or a fastening strap;
where the accelerometer sensors are mechanically decoupled in at least one direction;
measuring a skin surface acceleration with the accelerometer sensors;
wherein the accelerometer signal input is configured to combine signals from the array of accelerometer sensors to obtain the accelerometer signal from the skin surface acceleration;
obtaining a pulse-related signal of the patient from a pulse signal sensor;
obtaining patient information from a patient information source;
generating, by one or more computer processors, a template accelerometer signal that models accelerometer-based pulse palpation using the pulse-related signal as a reference signal and further using the patient information and context information indicating context of the acquisition of the accelerometer signal;
extracting, by the one or more computer processors, one or more features from the accelerometer signal by comparing the accelerometer signal to the generated template accelerometer signal;
detecting, by the one or more computer processors, the pulse and pulse strength of the patient from the one or more extracted features;
and display on the display a presence of the pulse and the pulse strength.

11. The method as claimed in claim 10, further comprising: detecting when the pulse is present;
and detecting at least one of a pulse arrival time or a pulse transit time as pulse-related information.

12. The method as claimed in claim 10, wherein the accelerometer signal is compared to the generated template accelerometer signal in three orthogonal directions.

13. The method as claimed in claim 10, wherein the pulse-related signal of the patient comprises a PPG signal, and wherein the context information comprises at least one of a posture, an activity, a motion, or a treatment phase of the patient.

14. A non-transitory computer readable medium storing instructions for reducing motion artefacts in a detection of at least one of pulse or pulse-related information of a patient that, wherein when executed by the one or more computer processors, the instructions cause the one or more computer processors to:
receive an accelerometer signal acquired by an array of accelerometer sensors arranged at skin of the patient;
wherein the accelerometer sensors are configured to directly contact the skin via an adhesive layer or a fastening strap;
where the accelerometer sensors are mechanically decoupled in at least one direction;
measure a skin surface acceleration with the accelerometer sensors;
combine signals from the array of accelerometer sensors to obtain the accelerometer signal from the skin surface acceleration;
receive a pulse-related signal of the patient from a pulse signal sensor;
receive patient information from a patient information source;
generate a template accelerometer signal that models accelerometer-based pulse palpation using the pulse-related signal as a reference signal and further using the patient information and context information indicating context of the acquisition of the accelerometer signal;
extract one or more features from the accelerometer signal by comparing the accelerometer signal to the generated template accelerometer signal;
determine the pulse and pulse strength of the patient from the one or more extracted features;
and display on the display a presence of the pulse and the pulse strength.

15. The non-transitory computer readable medium as claimed in claim 14, the instructions further cause the one or more computer processors to: detect when the pulse is present;
and detect at least one of a pulse arrival time or a pulse transit time as pulse-related information.

16. The non-transitory computer readable medium as claimed in claim 14, wherein the one or more computer processors compare the accelerometer signal to the generated template accelerometer signal in three orthogonal directions.

17. The non-transitory computer readable medium as claimed in claim 14, wherein the pulse-related signal of the patient comprises a PPG signal, and wherein the context information comprises at least one of a posture, an activity, a motion, or a treatment phase of the patient.

* * * * *